United States Patent
Barrus et al.

(10) Patent No.: US 9,271,763 B2
(45) Date of Patent: Mar. 1, 2016

(54) TRANSVERSE ROD CONNECTOR

(71) Applicant: K2M, Inc., Leesburg, VA (US)

(72) Inventors: Michael Barrus, Ashburn, VA (US);
Scott Jones, McMurray, PA (US);
Steven A. Brown, Timonium, MD (US)

(73) Assignee: K2M, LLC, Leesburg, VA (US)

(*) Notice: Subject to any disclaimer, the term of this patent is extended or adjusted under 35 U.S.C. 154(b) by 0 days.

(21) Appl. No.: 14/608,281

(22) Filed: Jan. 29, 2015

(65) Prior Publication Data
US 2015/0190179 A1 Jul. 9, 2015

Related U.S. Application Data

(62) Division of application No. 12/861,393, filed on Aug. 23, 2010, now Pat. No. 8,961,565.

(60) Provisional application No. 61/274,820, filed on Aug. 21, 2009.

(51) Int. Cl.
*A61B 17/70* (2006.01)

(52) U.S. Cl.
CPC ......... *A61B 17/7052* (2013.01); *A61B 17/7032* (2013.01); *A61B 17/7037* (2013.01)

(58) Field of Classification Search
CPC ........... A61B 17/7007; A61B 17/7008; A61B 17/7049–17/7052
USPC .................................................. 606/250–253
See application file for complete search history.

(56) References Cited

U.S. PATENT DOCUMENTS

| | | | |
|---|---|---|---|
| 4,611,582 A * | 9/1986 | Duff .............................. | 606/258 |
| 5,601,552 A | 2/1997 | Cotrel | |
| 6,136,003 A | 10/2000 | Hoeck et al. | |
| 6,264,658 B1 | 7/2001 | Lee et al. | |
| 6,283,967 B1 | 9/2001 | Troxell et al. | |
| 6,554,832 B2 | 4/2003 | Shluzas | |
| 7,122,036 B2 | 10/2006 | Vanacker | |
| 7,645,294 B2 | 1/2010 | Kalfas et al. | |
| 7,717,939 B2 | 5/2010 | Ludwig et al. | |
| 7,967,845 B2 | 6/2011 | Lauryssen et al. | |
| 8,961,565 B2 | 2/2015 | Barrus et al. | |
| 2002/0007183 A1* | 1/2002 | Lee et al. ......................... | 606/61 |
| 2002/0169448 A1 | 11/2002 | Vanacker | |
| 2003/0114853 A1 | 6/2003 | Burgess et al. | |
| 2004/0092931 A1 | 5/2004 | Taylor et al. | |
| 2005/0228377 A1 | 10/2005 | Chao et al. | |
| 2006/0064091 A1 | 3/2006 | Ludwig et al. | |
| 2006/0217712 A1 | 9/2006 | Mueller et al. | |
| 2006/0247626 A1 | 11/2006 | Taylor et al. | |
| 2007/0270808 A1 | 11/2007 | Drewry et al. | |
| 2008/0109039 A1* | 5/2008 | Michielli et al. .............. | 606/251 |
| 2009/0043339 A1 | 2/2009 | Tepper et al. | |

* cited by examiner

*Primary Examiner* — Jerry Cumberledge
*Assistant Examiner* — Nicholas Plionis
(74) *Attorney, Agent, or Firm* — Carter, DeLuca, Farrell & Schmidt, LLP

(57) ABSTRACT

A transverse rod connector includes an elongate member having first and second ends and first and second connection members. The first and second connection members are connected with first and second ends, respectively. The first and second connection members are configured for multidirectional positioning with respect to the elongate member. The first and second connection members are each dimensioned to be selectively and releasably secured to a bone anchor.

19 Claims, 12 Drawing Sheets

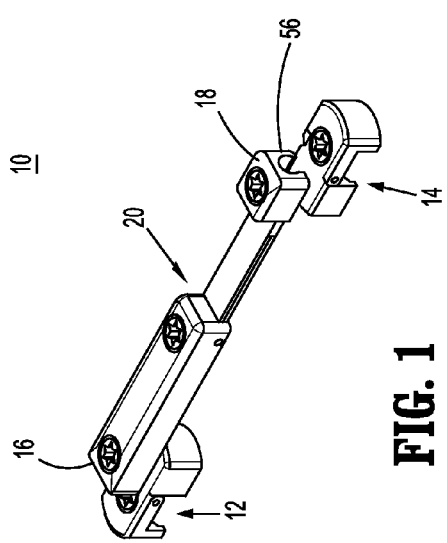
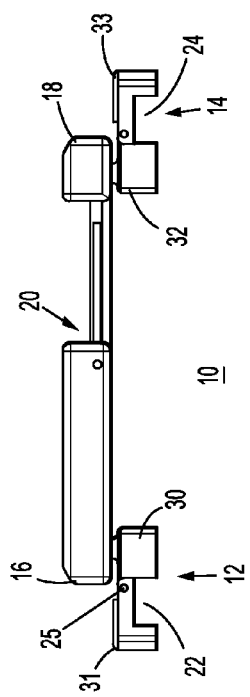
FIG. 1
FIG. 2

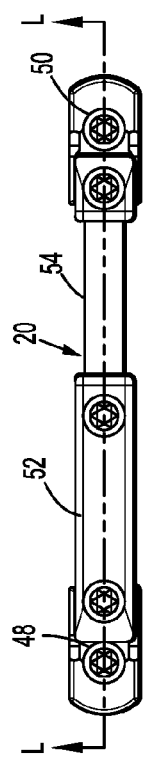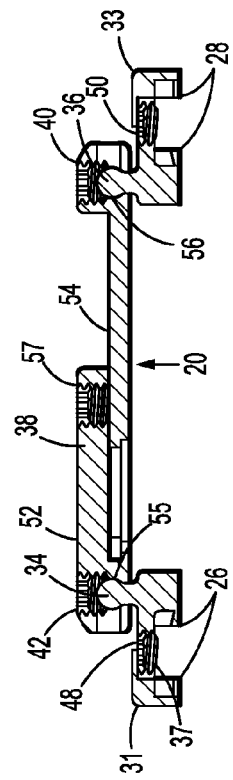

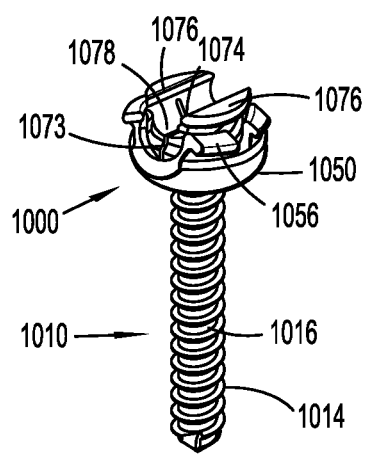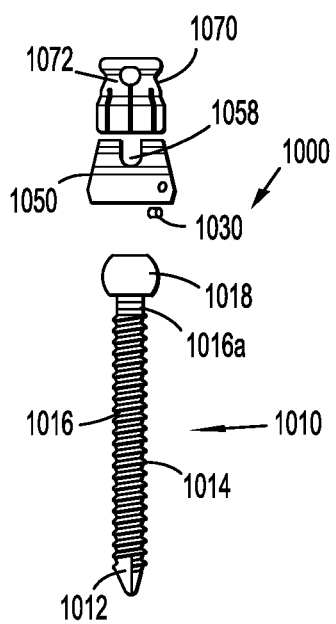
FIG. 21A  FIG. 21B

TRANSVERSE ROD CONNECTOR

CROSS-REFERENCE TO RELATED APPLICATION

This application is a division of U.S. patent application Ser. No. 12/861,393, filed on Aug. 23, 2010, which claims the benefit of U.S. Provisional Pat. Appl. Ser. No. 61/274,820, filed Aug. 21, 2009, the entire disclosure of each of which is incorporated by reference herein.

TECHNICAL FIELD

The present disclosure relates to a device for interconnecting bone anchors and, more particularly, to a transverse rod connector configured for multidirectional articulation with respect to the bone anchor.

BACKGROUND

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases. Many of these apparatuses commonly use a pair of longitudinal rods running in a relatively parallel relationship to each other and the spinal column. These rods are connected to coupling elements, which in turn are secured to the underlying vertebral bone by spinal bone fixation fasteners such as pedicle screws, hooks, and the like. The pair of longitudinal rods can be held in position relative to one another by transverse connectors, also known as transverse bridge elements or cross-connectors.

As the technology of spinal surgery has developed and improved, each of the spinal fixation components has also undergone improvements and modifications to address the shortcomings of conventional spinal fixation components. The natural anatomical variations in the spinal column of a subject are such that implanted spinal rods, while approximating a parallel relationship one to the other, can vary from that parallel relationship considerably and in multiple planes. For this reason, any transverse connector used to attach the two rods to each other should not be of a rigid design without the ability to be re-configured as needed during the process of implanting and attaching to the two opposing rods. While some improvements have been made in the articulation and re-configuration operation of transverse connectors during the implantation and rod connection process, a continuing need exists to provide an improved multidirectional articulating transverse connector that can adapt to a wide variance in the contours of the spinal column. Further, a need exists to provide such a transverse connector that can provide a secure attachment means to the spinal construct, most specifically in the posterior cervical spine region where a conventional cross connector cannot be inserted due to the short distance between bone anchor heads.

Conventional efforts to meet this need have fallen short of the desired transverse connector configuration. For example, U.S. Patent Publication No. 2006/0064091 to Ludwig includes first and second connector members for connection to the respective first and second bone anchors. The two connector members are connected one to the other by a fixed member, thereby not allowing adjustment between the connector members to accommodate the anatomy. In addition, the fixed member does not provide rotational freedom and needs to be bent into the appropriate configuration prior to attaching to the bone anchor.

For reasons discussed above, a continuing need exists for a transverse rod connector that provides ease of operation by the surgeon to simultaneously adjust in multiple dimensions one bone anchor connecting end of the system in relation to the other bone anchor connecting end of the system and to provide a device having secure attachment means to the bone anchor of the spinal construct.

SUMMARY

In accordance with an embodiment of the present disclosure, there is provided a transverse rod connector including, an elongate member and first and second connection members. The elongate member includes first and second ends and may be longitudinally adjustable. The first and second connection members are connected with the first and second ends of the elongate member, respectively. The first and second connection members are configured for multidirectional positioning with respect to the elongate member. The first and second connection members are each dimensioned to be selectively and releasably secured to a bone anchor.

In an embodiment, the first and second connection members may each include a base portion and a closing portion. The base portion and the closing portion may define a connection passage for receiving the bone anchor. Further, the base portion and the closing portion may be hingedly connected.

In another embodiment, the first and second connection members may each define an opening. In addition, the opening may align with the bone anchor when the bone anchor is received in the connection passage. The first and second connection members may each include a screw dimensioned to be received in the opening. The screws may couple the first and second connection members with bone anchors.

In yet another embodiment, the first and second ends of the elongate members may each include a receptacle portion. The first and second connection members may each include a ball joint. The ball joints may be received in the respective receptacle portions for multidirectional positioning of the first and second connection members with respect to the elongate member. The elongate member may include first and second screws dimensioned to be received in the respective receptacle portions. The first and second screws may securely fix the ball joints in the respective receptacle portions to fix the orientation of the connection members with respect to the elongate member.

In still another embodiment, the first and second ends of the elongate members may each include a ball joint. The first and second connection members may each include a socket portion. The ball joints may be received in the respective socket portions for multidirectional positioning of the first and second connection members with respect to the elongate member. The first and second connection members may each include a screw dimensioned to be received in the socket portion. The screws may securely fix the ball joints in the socket portions to adjustably fix the orientation of the respective connection members with respect to the elongate member.

In still another embodiment, the elongate member may include first and second portions longitudinally translatable with respect to each other. The first and second portions may at least partially overlap each other. The elongate member may define a through hole. The elongate member may further include a screw dimensioned to be received in the through hole. The screw may securely fix the position of the first and second portions with respect to each other.

In accordance with another embodiment of the present disclosure, there is provided a transverse rod connector including, an elongate member and first and second connection members. The elongate member includes first and second ends. The first and second connection members are connected with first and second ends, respectively. The first and second connection members are selectively and releasably secured to bone anchors, respectively. The first and second connection members each include a stationary portion and a sliding portion. The stationary portion and the sliding portion define a connection passage. The sliding portion is movable to adjust the dimensions of the connection passage.

In an embodiment, the first and second connection members may each define a receptacle portion dimensioned to receive a screw for coupling bone anchors to respective first and second connection members. The receptacle portion may be defined in the sliding portion of the first and second connection members. In addition, the first and second ends of the elongate member may each define an opening dimensioned to receive the screw. The opening may be dimensioned for longitudinal movement of the screw with respect to the elongate member when the screw is securely fixed to the receptacle portion. Further, the elongate member may be arched. The elongate member may further include screw caps for fastening elongate member against the first and second connection members.

BRIEF DESCRIPTION OF THE DRAWINGS

The foregoing and other features of the transverse rod connector will become apparent to one skilled in the art to which the disclosed system and devices relate upon consideration of the following description of exemplary embodiments with reference to the accompanying drawings, wherein:

FIG. 1 is a perspective view of a transverse rod connector in accordance with an embodiment of the present disclosure;

FIG. 2 is an end view of the transverse rod connector of FIG. 1;

FIG. 3 is a top view of the transverse rod connector of FIG. 1;

FIG. 4 is a cross-sectional end view of the embodiment of FIG. 3 taken along section line L-L;

FIG. 21A is a perspective view of a bone anchor for use with the transverse rod connector of FIG. 17; and FIG. 21B is a side view of the bone anchor of FIG. 21A with parts separated.

DETAILED DESCRIPTION

Figure 5A:
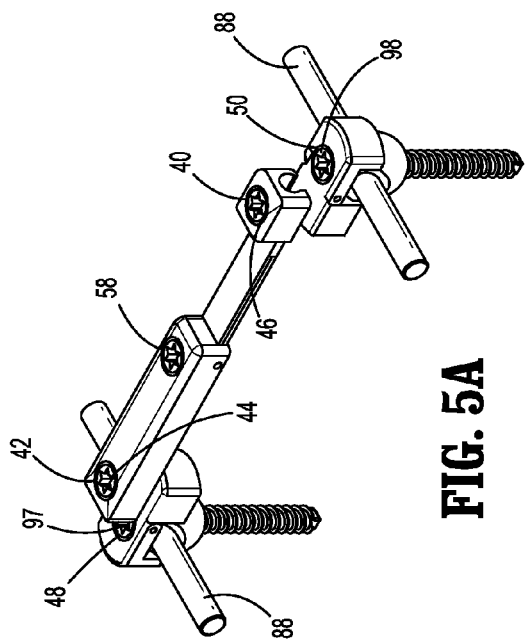
FIG. 5A is a perspective view of the transverse rod connector of FIG. 1 coupled to bone anchors in an extended position.

Various embodiments of the presently disclosed transverse rod connector will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

The presently disclosed transverse rod connector is generally shown as reference numeral 10 in FIG. 1. Transverse rod connector 10 includes a cross member assembly 20 and first and second connection members 12, 14. The first and second connection members 12, 14 are disposed at opposing ends 16, 18 of the device 10, respectively. The two connection members 12, 14 are each configured to be selectively and releasably secured to a bone anchor 1000, which in turn can be secured to a subject's vertebra or other bone structure. Connection members 12, 14, however, may be configured to couple with other securement structures such as bone pins.

As shown in FIGS. 21A and 21B, bone anchor 1000 may include a pedicle screw 1010, a pin 1030, a coupling 1050 and a collet 1070. Coupling 1050 may define a saddle 1058 having a generally U-shaped configuration. Saddle 1058 is configured and dimensioned for receiving a rod 88 shown in FIGS. 5A, 5B, 6A, 6B, 13 and 14. Rod 88 may be used in any or all of the disclosed embodiments. In addition, coupling 1050 may also include a plurality of fingers 1056 extending radially outward. Collet 1070 includes a generally cylindrical body portion 1072 with an opening 1074 extending axially therethrough and a pair of upstanding wings 1076 that define a saddle 1078 which is also generally U-shaped. Body portion 1072 includes a slot 1073, and as such wings 1076 may flex toward and away from each other, whereby flexing of wings 1076 toward each other engages the outer surface of a rod 88 disposed in saddle 1078 to enable frictional securing of the rod 88.

Pedicle screw 1010 may include a shank 1016 having a helical thread 1014 formed thereon. A cutting portion 1012 is formed at a distal end of the pedicle screw 1010. A head 1018 is disposed at a proximal end of pedicle screw 1010 adjacent a neck portion 1016a. On the top surface of head 1018, an opening is formed. The opening may include configuration for receiving the operative end of a suitable driving tool.

Collet 1070 is seated atop head 1018 of pedicle screw 1010. The opening at the bottom of collet 1070 is dimensioned and configured for receiving head 1018. As such, collet 1070 and head 1018 are rotatable and pivotable in relation to each other, thereby allowing the pedicle screw 1010 to be repositioned in a plurality of orientations relative to collet 1070. Collet 1070 and pedicle screw 1010 are inserted into coupling 1050. Pin 1030 aligns collet 1070 and coupling 1050 for maintaining a fixed relationship therebetween. As assembled, pedicle screw 1010 is rotatable and pivotable in relation to collet 1070 and coupling 1050. Reference may be made to International Patent Application No. PCT/US2008/080682, filed on Apr. 23, 2010, entitled "POSTERIOR PEDICLE SCREW HAVING A TAPER LOCK," the entire disclosure of which is incorporated by reference herein.

As shown in FIG. 2, the connection members 12, 14 include base portions 30, 32 and closing portions 31, 33 that define first and second connection passages 22, 24 therebetween, respectively. Connection passages 22, 24 are opened medial-laterally at the first or second end 16, 18 of the device 10. The outermost edges of the respective medial-laterally opened connection passages 22, 24 can be configured to provide a retention feature 26, 28, as depicted in FIG. 4, for coupling or attaching to bone anchor 1000. The retention feature is configured as a hinge mechanism 25 (See FIGS. 2 and 5B) to facilitate attachment onto bone anchor 1000. Once bone anchor 1000 (for example fingers 1056 and/or wings 1076) has been captured by the retention features 26, 28, bone anchor locking screws 97, 98 are threaded into respective openings 48, 50 to couple first and second connection members 12, 14 to respective bone anchors 1000.

The first and second connection members 12, 14 define ball joint members 34, 36 at their most proximal ends 30, 32, respectively. Each of the ball joint members 34, 36 are configured to slide and drop into the ball joint receptacles 55, 56 of the cross member assembly 20. As shown in FIGS. 4 and 5B, connection members 12, 14 may each include a rigid ring member 37 that contains internal threads for coupling with the bone anchor locking screws 97, 98. This rigid ring member 37 may also contain a tab feature or other such member on the external diameter to mate with a bone anchor 1000 such that it prevents rotation of said bone anchor 1000.

As shown in FIG. 4, the upper surface 38 of the cross member assembly defines bone anchor locking screw receptacles 40, 42 which are sized and configured to receive a locking screw 44, 46. The bone anchor locking screw receptacles 40, 42 as best shown in FIG. 4 are provided with threads to secure the locking screws 44, 46 into place.

As shown in FIGS. 3 and 4, the cross member assembly 20 has two sliding portions 52, 54. Each sliding portion 52, 54 contains a ball joint receptacle 55, 56, and can slide freely with respect to each other. Once the desired distance between the two ball joint receptacles 55, 56 is obtained, a bone anchor locking screw 58 is attached to the bone anchor locking screw receptacle 57 to securely fix the cross member assembly 20 and lock it into position.

As shown in the non-limiting examples of FIGS. 1-4, any articulating surface of the device can be treated, machined, scored, or in any known manner textured to provide a roughened or textured surface that can serve to increase the locking contact of those surfaces when the articulating members are set in place and the associated locking screws are manipulated to lock the device in the desired configuration.

Figure 5B:
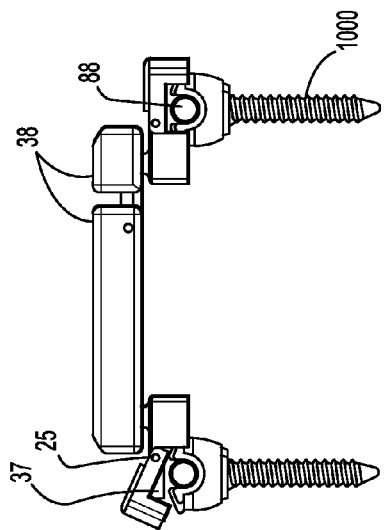
FIG. 5B is an end view of the transverse rod connector of FIG. 5A coupled to the bone anchors in a retracted position.

In operation, a user as indicated above can manipulate the device 10 into position relative to two opposing and relatively parallel bone anchors, independently connecting the first and second connection members 12, 14 to their respective bone anchors and adjusting the alignment of the member 12,14 with the centrally connected cross member assembly 20 by manipulating the respective first ball joint member 34 within the first ball joint receptacle 55 and the second ball joint member 36 with the second ball joint receptacle 56 and selecting the appropriate length of the cross member (see FIG. 5A). When all members of the device 10 are positioned in a desired orientation, the user can tighten the provided locking screws 44, 46, 58, and lock the device into a selected configuration relative to the two opposing bone anchors 1000. Adjustment or removal of the device can be easily achieved by loosening the locking screws 44, 46, 58.

Figure 6A:
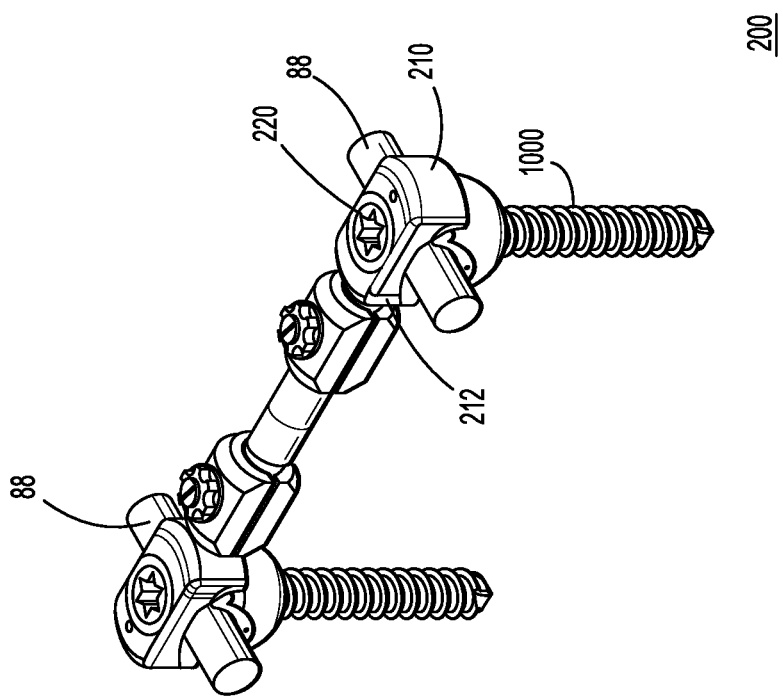
FIG. 6A is a perspective view of a transverse rod connector in accordance with another embodiment of the present disclosure.
Figure 6B:
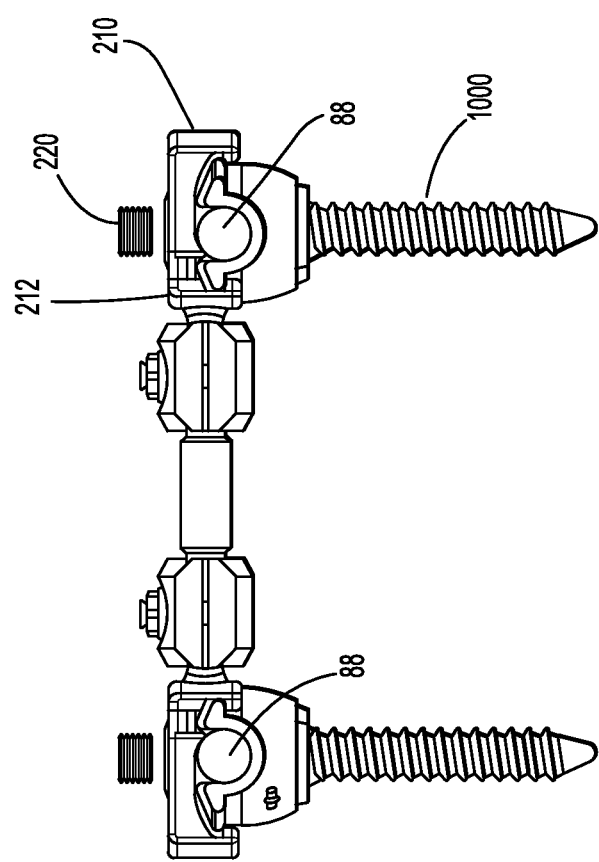
FIG. 6B is an end view of the transverse rod connector of FIG. 6A with screws separated.
Figure 7:
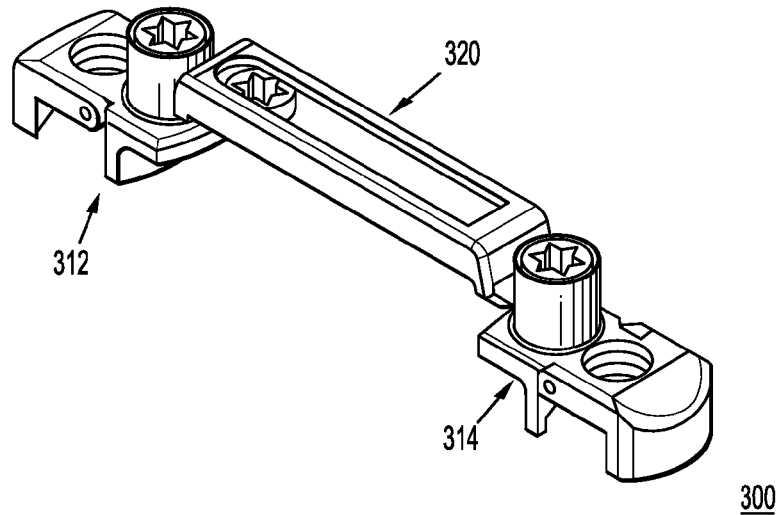
FIG. 7 is a perspective view of a transverse rod connector in accordance with another embodiment of the present disclosure.

As shown in FIGS. 6A and 6B, another embodiment 200 provides a two-part capture mechanism including a mobile portion 210 and a stationary portion 212 for retaining bone anchor 1000. The first portion captures one-half of bone anchor 1000 while the second half overlaps it to capture the remaining portion. FIG. 6B displays the open configuration of the transverse rod connector, whereby the lateral portion of the connection member slides laterally to allow for ease of attachment onto a bone anchor. The retaining feature of the stationary portion 212 and the retaining feature of the mobile portion 210 capture the bone anchor 1000. The stationary and mobile portions 210, 212 along with the bone anchor 1000 are retained by coupling of a bone anchor locking screw 220. This closed configuration is depicted in FIG. 6A.

With reference now to FIGS. 7-16, yet another embodiment of a transverse rod connector in accordance with the present disclosure, is illustrated. In the interest of brevity, the present embodiment will focus on the differences between the previously described transverse rod connectors 10, 200 and connector 300. Connector 300 includes a cross member assembly 320 and first and second connection members 312, 314. Each connection member 312, 314 is configured to be selectively and releasably secured to bone anchor 1000 which is secured to a subject's vertebra or other bone structure. Notably, connection member 312 defines an internal opening 348 therethrough and connection member 314 defines an internal opening 350 therethrough. Internal openings 348 and 350 may be threaded to facilitate engagement with a screw.

Figure 8:
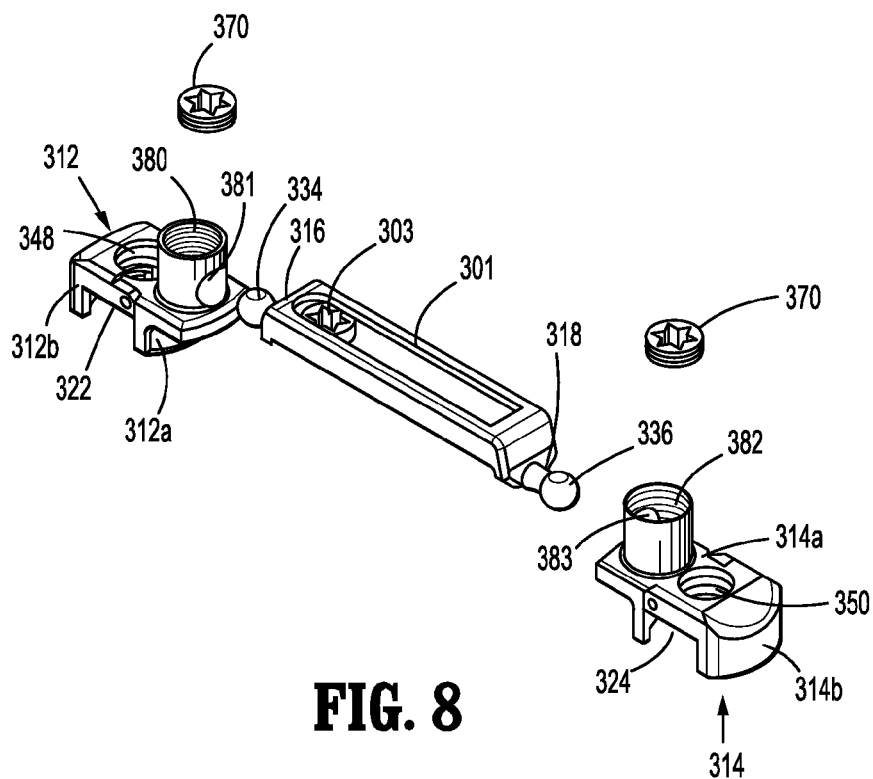
FIG. 8 is a perspective view of the transverse rod connector of FIG. 7 with parts separated.
Figure 9:
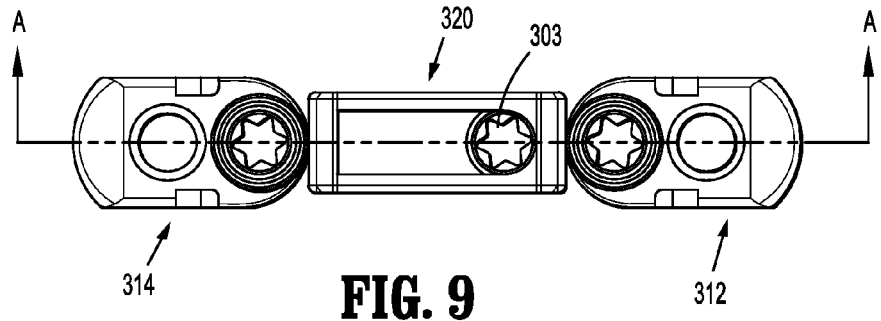
FIG. 9 is a top view of the transverse rod connector of FIG. 7 in a retracted position.
Figure 10:
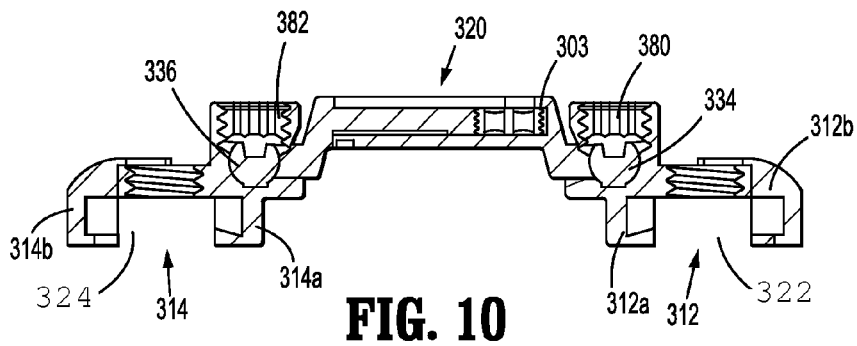
FIG. 10 is a cross-sectional end view of the embodiment of FIG. 9 taken along section line A-A.
Figure 11:
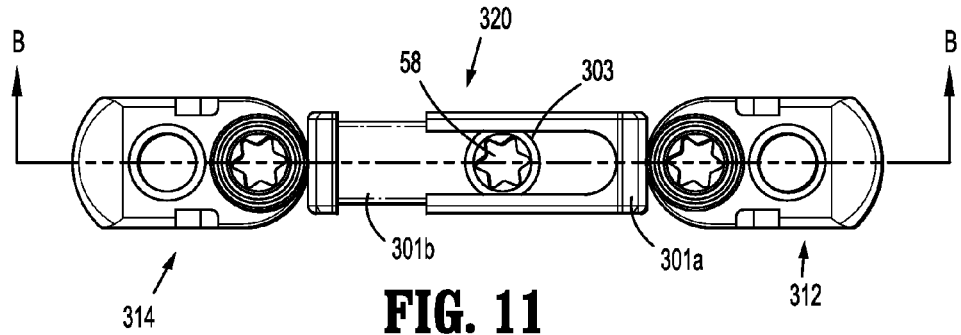
FIG. 11 is a top view of the transverse rod connector of FIG. 7 in an extended position.
Figure 12:
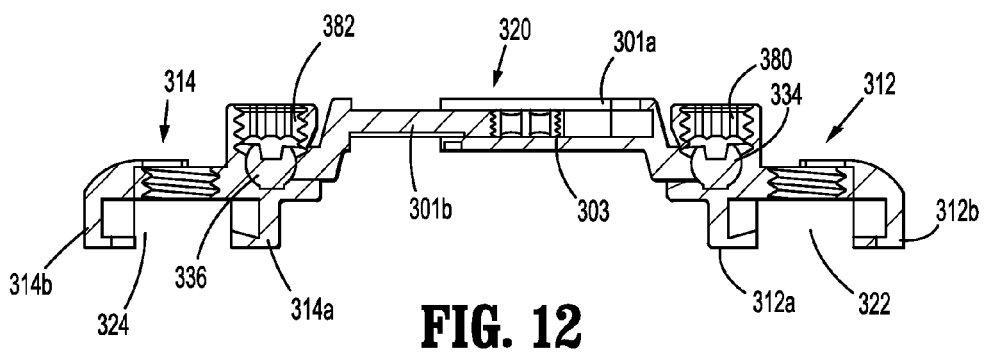
FIG. 12 is a cross-sectional end view of the embodiment of FIG. 11 taken along section line B-B.
Figure 13:
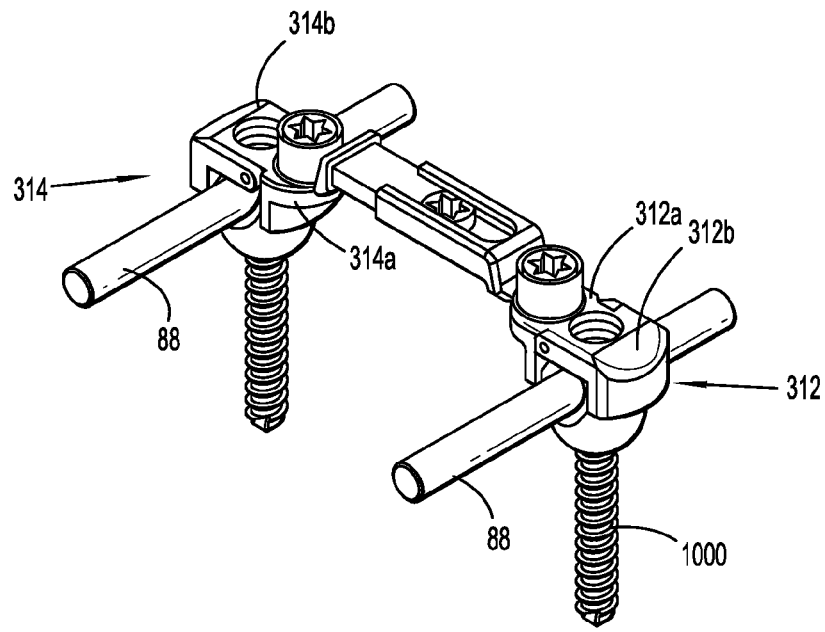
FIG. 13 is a perspective view of the transverse rod connector of FIG. 7 engaging bone anchors in an extended position.

As best shown in FIGS. 8, 10 and 12, cross member assembly 320 includes an elongate member 301 with first and second ends 316, 318. First and second ends 316, 318 include ball joint members 334, 336, respectively. In addition, elongate member 301 may include a first portion 301a and a second portion 301b. First and second portions 301a, 301b may be slidably coupled to enable reciprocating translation with respect to each other. (FIGS. 11 and 12 illustrate an extended position in which first and second portions 301a, 301b are at least partially overlapped). At least one of first and second portions 301a, 301b may define a threaded bore 303 to enable screw 58 to securely fix the relative position of first and second portions 301a, 301b, in order to meet the needs of a particular procedure being performed. As shown in FIGS. 8-12, second portion 301b defines such threaded bore 303 at an end portion thereof which remains at least partially overlapped with first portion 301a to fix the relative position with respect to each other.

Figure 14:
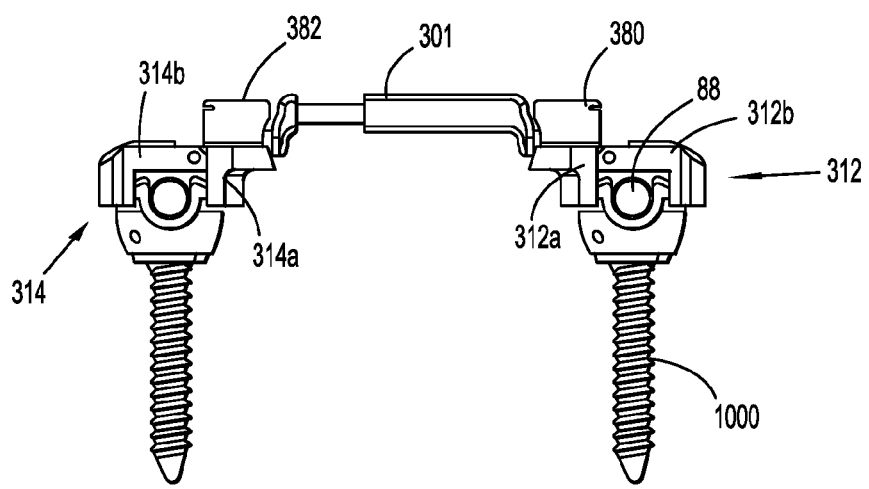
FIG. 14 is an end view of the transverse rod connector of FIG. 7 engaging bone anchors in an extended position.
Figure 15:
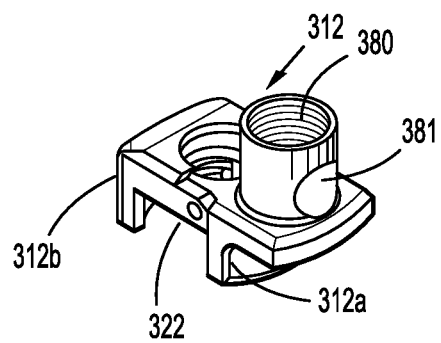
FIG. 15 is a perspective view of a connection member for use with the transverse rod connector of FIG. 7.
Figure 16:
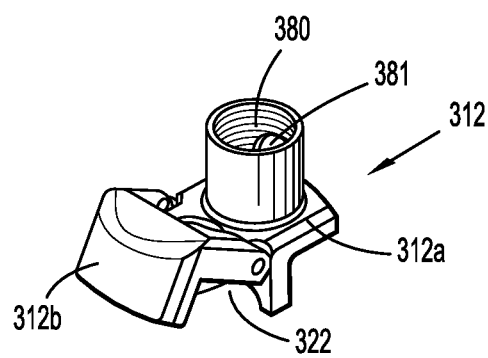
FIG. 16 is a perspective view of the connection member of FIG. 15 in an open configuration.

With reference now to FIGS. 14-16, connection members 312, 314 each include a base portion 312a, 314a and a closing portion 312b, 314b. Each connection member 312, 314 defines a connection passage 322, 324 dimensioned to receive bone anchor 1000. Respective closing portions 312b, 314b may be hingedly connected to base members 312a, 314a. In contrast to the previously described embodiments, each connection member 312, 314 includes a socket 380, 382 for receiving therein respective ball joint members 334, 336, as best illustrated in FIGS. 15 and 16. In particular, sockets 380, 382 each define respective openings 381, 383, through which ball joint members 334, 336 of elongate member 301 are received to form ball joints. Sockets 380, 382 may include internal threads for receiving screws 370. Screws 370 may be provided to securely fix ball joint members 334, 336 in sockets 380, 382. As such, the relative position/orientation of elongate member 301 and connection members 312, 314 may be adjusted to meet the needs of the particular procedure being performed. Operation of transverse rod connector 300 is substantially similar to connector systems 10, 200 described hereinabove, and will be omitted in the interest of brevity.

With reference now to FIGS. 17-20, a connector system 400 in accordance with still another embodiment of the present disclosure is illustrated. In the interest of brevity, the present embodiment will focus on the differences between the previously described transverse rod connectors 10, 200, 300 and connector system 400. Connector system 400 includes an elongate member 401 and first and second connection members 412, 414. Each of connection members 412, 414 may be selectively and releasably secured to bone anchor 1000 which is secured to a subject's vertebra or other bone structure.

Figure 17:
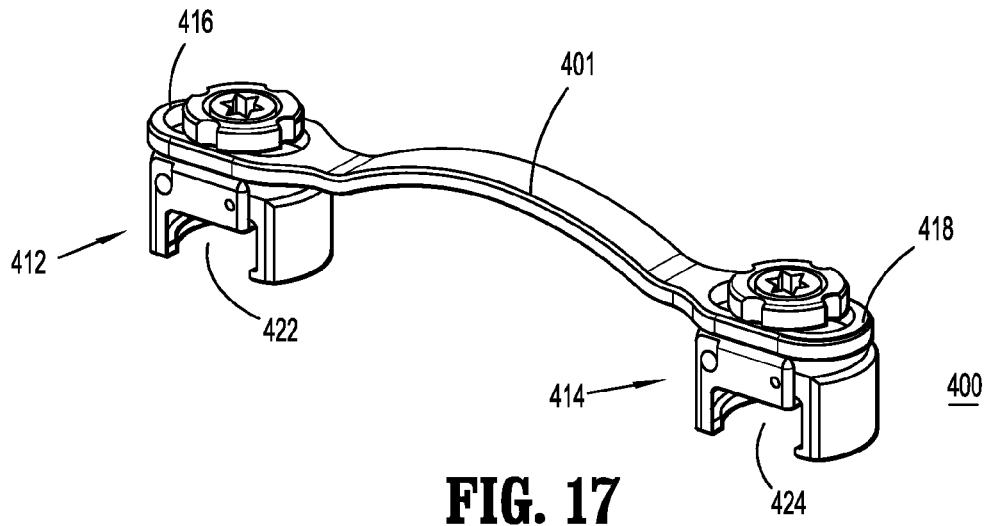
FIG. 17 is a perspective view of a transverse rod connector in accordance with another embodiment of the present disclosure.
Figure 18:
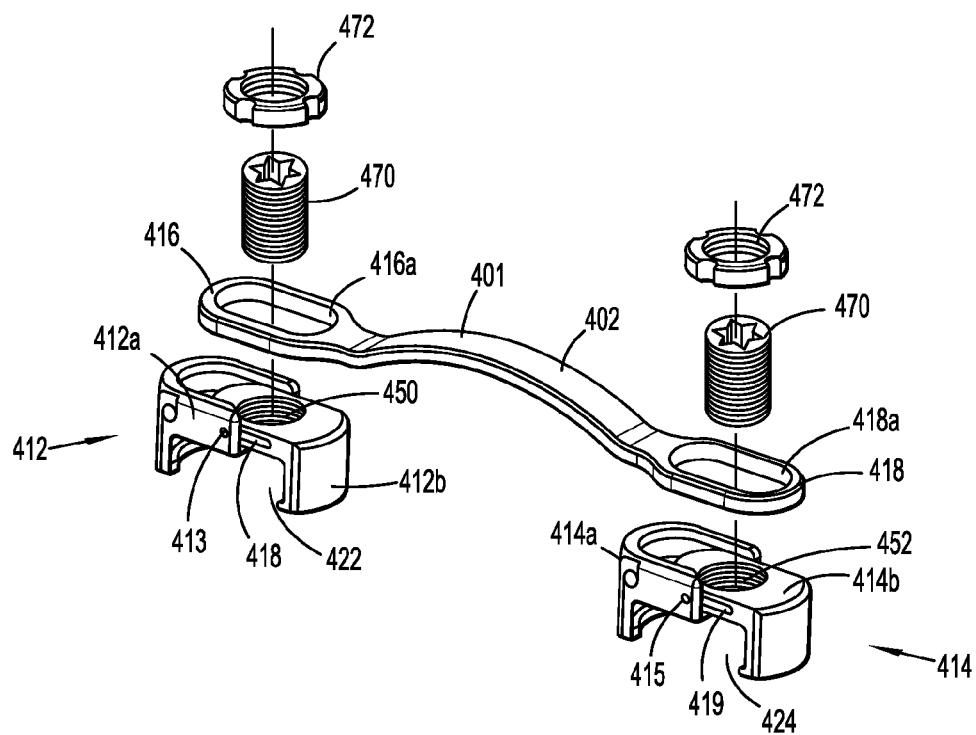
FIG. 18 is a perspective view of the transverse rod connector of FIG. 17 with parts separated.
Figure 19:
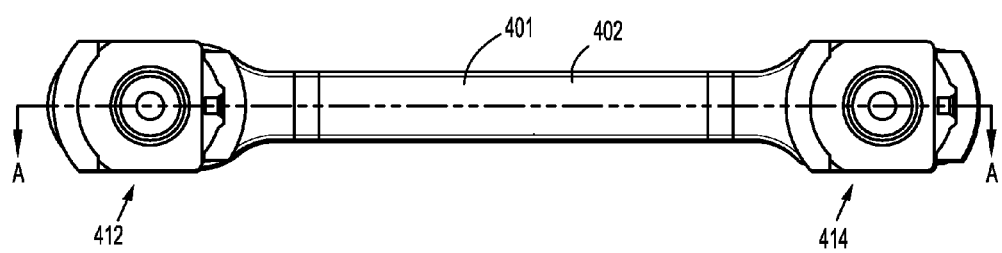
FIG. 19 is a top view of the transverse rod connector of FIG. 17.
Figure 20:
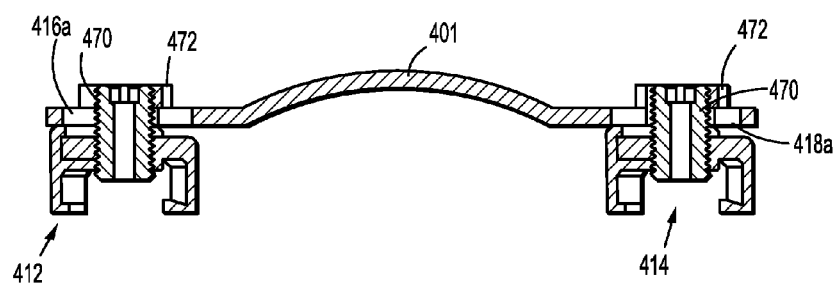
FIG. 20 is a cross-sectional end view of the embodiment of FIG. 19 taken along section line A-A.

Elongate member 401 includes a body portion 402 which may be arched as shown in FIGS. 17, 18 and 20 and receiving end portions 416, 418. Receiving end portions 416, 418 each define an opening 416a, 418a dimensioned to receive a screw 470. Openings 416a, 418a may also be dimensioned to enable adjustment of the distance between connection members 412, 414, as will be described below.

Connection members 412, 414 each include a stationary portion 412a, 414a and a sliding portion 412b, 414b, as best seen in FIG. 18. Each stationary portion 412a, 414a includes at least one lateral pin 413, 415 slidably received within respective longitudinal slots 418, 419 defined in respective sliding portions 412b, 414b. Such configuration enables reciprocating movement of sliding portions 412b, 414b to and from stationary portions 412a, 414a, which in turn enables connection passages 422, 424 to be adjusted to facilitate attachment/coupling to bone anchor 1000. In addition, each sliding portion 412b, 414b includes an internal opening 450, 452 for receiving screw 470. Internal openings 450, 452 may be threaded to facilitate engagement with screw 470.

In contrast to the above embodiments, screw 470 is utilized to couple the respective bone anchors 1000 to first and second connection members 412, 414 and to adjustably fix the distance between first and second connection members 412, 414. Under such configuration, connection passages 422, 424 are first adjustably enlarged by moving sliding portions 412b, 414b away from respective stationary portions 412a, 414a, and bone anchors 1000 are placed in respective connection passages 422, 424. Upon placement of bone anchors 1000 in connection passages 422, 424, screws 470 may be attached to respective internal openings 450, 452 and couple connection members 412, 414 onto bone anchors 1000. At this time, elongate member 401 is placed above connection members 412, 414 and screws 470 extend out of respective openings 416a, 418a. While connection members 412, 414 are coupled onto respective bone anchors 1000, the distance between connection members 412, 414 may still be adjusted. Upon determining the desired distance, caps 472 may be utilized to securely fix the distance between connection members 412, 414 by fastening caps 472 against elongate member 401, as best shown in FIG. 17.

The devices 10, 200, 300, 400 can be manufactured as components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose. It is also conceivable that some components of the device can be made from plastics, composite materials, and the like.

It is also within the concept of the inventors to provide a kit, which includes at least one of the transverse rod connectors. The kit can also include additional orthopedic devices and instruments; such as for example, instruments for tightening or loosening the locking screws, spinal rods, hooks or links and any additional instruments or tools associated therewith. Such a kit can be provided with sterile packaging to facilitate opening and immediate use in an operating room.

It will be understood that various modifications may be made to the embodiments of the presently disclosed transverse rod connector. Therefore, the above description should not be construed as limiting, but merely as exemplifications of embodiments. Those skilled in the art will envision other modifications within the scope and spirit of the present disclosure.

The invention claimed is:

1. A transverse rod connector comprising:
   a cross member having a first end and a second end, the cross member defining a longitudinal axis that extends between a pair of ball joint receptacles, a first one of the pair of ball joint receptacles defined on the first end of the cross member and a second one of the pair of ball joint receptacles defined on the second end of the cross member; and
   a pair of connection members, each connection member of the pair of connection members including a ball joint member that is slidably movable along the longitudinal axis of the cross member with the ball joint member received within one ball joint receptacle of the pair of ball joint receptacles of the cross member to secure one connection member of the pair of connection members to the cross member, each connection member of the pair of connection members including a base portion and a closing portion, the base portion and the closing portion defining a connection passage therebetween, the base portion and the closing portion being hingedly connected such that pivotal movement of the closing portion relative to the base portion enables selective and releasable receipt of a bone anchor within the connection passage to secure the bone anchor therein.

2. The transverse rod connector of claim 1, wherein the cross member includes a first sliding portion positioned to slide relative to a second sliding portion.

3. The transverse rod connector of claim 2, wherein the first sliding portion defines a locking screw receptacle adapted to receive a locking screw to lock the first and second sliding portions together in fixed relation to each other.

4. The transverse rod connector of claim 2, wherein each sliding portion defines a locking screw receptacle adapted to receive a locking screw, the locking screw being engagable with the ball joint member of a respective connection member to fix an orientation of the respective connection member relative to the cross member.

5. The transverse rod connector of claim 1, wherein the connection passage is opened medial-laterally.

6. The transverse rod connector of claim 1, wherein a length of the cross member is selectively adjustable.

7. The transverse rod connector of claim 1, wherein the pair of connection members is rotatable relative to the cross member while the ball joint members of the pair of connection members are received within the pair of ball joint receptacles of the cross member.

8. The transverse rod connector of claim 1, wherein the pair of connection members is side-loaded onto the cross member.

9. A transverse rod connector system comprising:
a bone anchor; and
a transverse rod connector including:
  a cross member extending longitudinally between first and second end faces, the cross member defining a ball joint receptacle in at least one of the first and second end faces; and
  a connection member including a ball joint member that is received within the ball joint receptacle of the cross member to secure the connection member to the cross member, the connection member including a base portion and a closing portion, the base portion and the closing portion defining a connection passage therebetween, the base portion and the closing portion being hingedly connected such that pivotal movement of the closing portion relative to the base portion enables selective and releasable receipt of the bone anchor within the connection passage to secure the bone anchor therein.

10. The transverse rod connector system of claim 9, wherein the cross member includes a first sliding portion positioned to slide relative to a second sliding portion.

11. The transverse rod connector system of claim 10, wherein the first sliding portion defines a locking screw receptacle adapted to receive a locking screw to lock the first and second sliding portions together in fixed relation to each other.

12. The transverse rod connector system of claim 10, wherein each sliding portion defines a locking screw receptacle adapted to receive a locking screw, the locking screw being engagable with the ball joint member of a respective connection member to fix an orientation of the respective connection member relative to the cross member.

13. The transverse rod connector system of claim 9, wherein the connection passage is opened medial-laterally.

14. The transverse rod connector system of claim 9, wherein a length of the cross member is selectively adjustable.

15. The transverse rod connector system of claim 9, wherein the connection member is rotatable relative to the cross member while the ball joint member is received within the ball joint receptacle of the cross member.

16. The transverse rod connector system of claim 9, wherein the connection member is side-loaded onto the cross member.

17. The transverse rod connector system of claim 9, further including a spinal rod, wherein the bone anchor includes a threaded shank and a saddle coupled to the threaded shank, the threaded shank configured to be secured to bone, the saddle configured to receive the spinal rod.

18. A transverse rod connector system for coupling to a pair of bone anchors, the transverse rod connector system comprising:
a first bone anchor;
a second bone anchor;
a cross member defining a pair of ball joint receptacles on opposite ends thereof;
a first connection member including a ball joint member that is received within one ball joint receptacle of the pair of ball joint receptacles of the cross member to secure the first connection member to the cross member, the first connection member including a base portion and a closing portion, the base portion and the closing portion defining a connection passage therebetween, the base portion and the closing portion being hingedly connected such that pivotal movement of the closing portion relative to the base portion enables selective and releasable receipt of the first bone anchor within the connection passage to secure the first bone anchor therein; and
a second connection member secured to the other ball joint receptacle of the pair of ball joint receptacles of the cross member, the second connection member configured to selectively and releasably secure to the second bone anchor;
wherein the cross member extends longitudinally between first and second end faces, and wherein at least one ball joint receptacle of the pair of ball joint receptacles is defined in one of the first and second end faces of the cross member.

19. The transverse rod connector system of claim 18, wherein the at least one of the first and second connection members can be side-loaded into the cross member.

* * * * *